(12) United States Patent
Kressel et al.

(10) Patent No.: US 10,933,240 B2
(45) Date of Patent: Mar. 2, 2021

(54) TREATMENT OF INFLAMMATION BY SELECTIVE DMV CHOLINERGIC NEURON STIMULATION

(71) Applicant: THE FEINSTEIN INSTITUTES FOR MEDICAL RESEARCH, Manhasset, NY (US)

(72) Inventors: Adam M. Kressel, Plainview, NY (US); Valentin A. Pavlov, Bayside, NY (US); Sangeeta S. Chavan, Syosset, NY (US); Kevin J. Tracey, Old Greenwich, CT (US)

(73) Assignee: The Feinstein Institutes for Medical Research, Manhasset, NY (US)

(*) Notice: Subject to any disclaimer, the term of this patent is extended or adjusted under 35 U.S.C. 154(b) by 69 days.

(21) Appl. No.: 16/272,295

(22) Filed: Feb. 11, 2019

(65) Prior Publication Data

US 2019/0247659 A1 Aug. 15, 2019

Related U.S. Application Data

(60) Provisional application No. 62/629,149, filed on Feb. 12, 2018.

(51) Int. Cl.
*A61N 1/36* (2006.01)
*A61N 1/05* (2006.01)
*A61N 1/04* (2006.01)

(52) U.S. Cl.
CPC ....... *A61N 1/36053* (2013.01); *A61N 1/0412* (2013.01); *A61N 1/0536* (2013.01); *A61N 1/3615* (2013.01); *A61N 1/0504* (2013.01)

(58) Field of Classification Search
CPC .. A61N 1/0412; A61N 1/0456; A61N 1/0504; A61N 1/0536; A61N 1/36014; A61N 1/36053; A61N 1/3615; A61N 2005/067; A61N 5/0622
See application file for complete search history.

(56) References Cited

U.S. PATENT DOCUMENTS

| | | | |
|---|---|---|---|
| 2013/0131753 A1* | 5/2013 | Simon | A61N 1/36007 607/40 |
| 2013/0237550 A1* | 9/2013 | Toler | A61K 31/506 514/256 |
| 2014/0243714 A1* | 8/2014 | Ward | A61B 5/4836 601/2 |
| 2014/0288551 A1* | 9/2014 | Bharmi | A61N 1/36121 606/41 |

OTHER PUBLICATIONS

Martelli et al., "Reflex Control of Inflammation by Sympathetic Nerves, Not the Vagus," J. Physiol., vol. 592.7, Jan. 13, 2014, pp. 1677-1686.

* cited by examiner

*Primary Examiner* — George Manuel
(74) *Attorney, Agent, or Firm* — Amster, Rothstein & Ebenstein LLP

(57) ABSTRACT

Methods for electrical modulation of inflammation or serum TNF levels in a subject.

7 Claims, 4 Drawing Sheets

TREATMENT OF INFLAMMATION BY SELECTIVE DMV CHOLINERGIC NEURON STIMULATION

CROSS-REFERENCE TO RELATED APPLICATIONS

This application claims benefit of U.S. Provisional Application No. 62/629,149, filed Feb. 12, 2018, the contents of which are hereby incorporated by reference.

STATEMENT OF GOVERNMENT SUPPORT

This invention was made with government support under grant number GM128008 awarded by the National Institutes of Health. The government has certain rights in the invention.

BACKGROUND OF THE INVENTION

The disclosures of all publications, patents, patent application publications and books referred to in this application are hereby incorporated by reference in their entirety into the subject application to more fully describe the art to which the subject invention pertains.

The vagus nerve is composed of fibers originating from both the dorsal motor nucleus (DMV) and nucleus ambiguus (NA) (23, 24). Very few studies have investigated the role of fibers originating in these brainstem nuclei to the inflammatory reflex (25, 26). Additionally, previous studies involving vagus nerve stimulation have relied on electrically stimulating the whole vagus nerve bundle (4, 5), a non-specific method that does not discriminate between individual fiber types that contribute to the anti-inflammatory effect.

The present invention addresses the need for additional therapis for inflammatory pathologies based on newly identified neuronal influences.

SUMMARY OF THE INVENTION

A method of suppressing or ameliorating inflammation in a subject comprising electrically modulating cholinergic neurons in a dorsal motor nucleus of a vagal nerve of subject effective to suppress or ameliorate inflammation in a subject.

A method of suppressing or reducing serum TNF levels in a subject experiencing inflammation comprising electrically modulating cholinergic neurons in a dorsal motor nucleus of a vagal nerve of subject effective to suppress or reduce serum TNF levels in a subject. A method of artificially reducing TNF release by splenic macrophages expressing α7nAChR in a subject comprising electrically modulating cholinergic neurons in a dorsal motor nucleus of a vagal nerve of subject effective to reduce TNF release by splenic macrophages expressing α7nAChR.

A method of enhancing an inflammatory response in a subject comprising electrically inhibiting activity of cholinergic neurons in a dorsal motor nucleus of a vagal nerve of the subject effective to enhance an inflammatory response in a subject.

A method of increasing serum TNF levels in a subject comprising electrically inhibiting activity of cholinergic neurons in a dorsal motor nucleus of a vagal nerve of the subject effective to increase serum TNF levels in a subject.

DETAILED DESCRIPTION OF THE INVENTION

Figure 1:
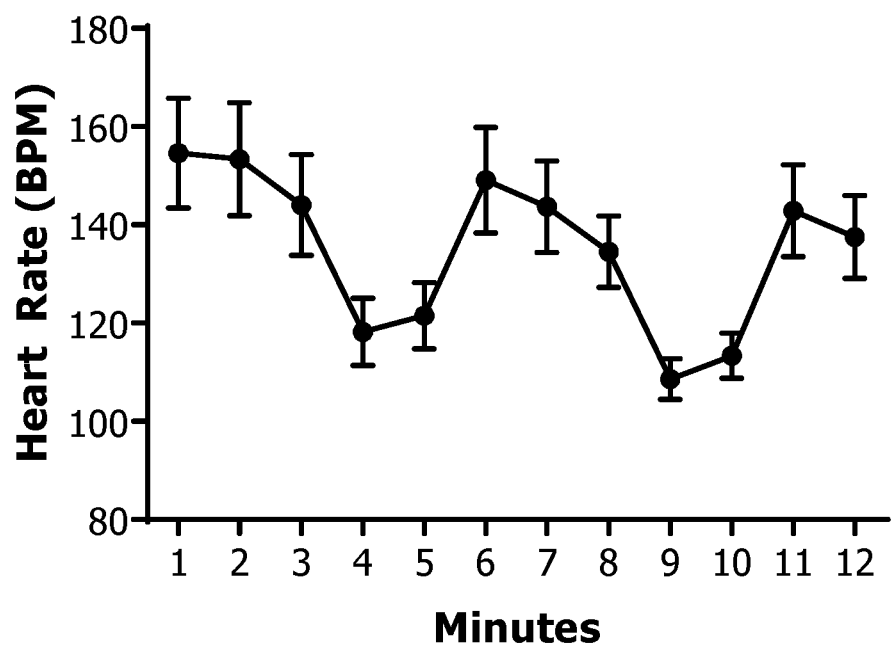
FIG. 1: A 200 μm fiber optic probe was inserted into the DMV of ChAT-ChR2-EYFP mice and light was applied (473 nm, 20 Hz, 25% duty cycle, 2 minutes). Simultaneous EKG recordings were obtained. During optogenetic stimulation, heart rate decreased (n=10).

A method of suppressing or ameliorating inflammation in a subject comprising electrically modulating cholinergic neurons in a dorsal motor nucleus of a vagal nerve of subject effective to suppress or ameliorate inflammation in a subject.

A method of suppressing or reducing serum TNF levels in a subject experiencing inflammation comprising electrically modulating cholinergic neurons in a dorsal motor nucleus of a vagal nerve of subject effective to suppress or reduce serum TNF levels in a subject.

In embodiments, the serum TNF levels are suppressed or reduced and result totally from, or in part from, splenic nerve activity.

In embodiments, the electrically modulating comprises stimulating the cholinergic neurons in a dorsal motor nucleus of the vagal nerve.

In embodiments, the cholinergic neurons are selectively stimulated.

In embodiments, vagal nerve activity is induced.

In embodiments, splenic nerve activity is induced.

In embodiments, the method effects an increase in splenic norepinephrine release.

In embodiments, the subject is human.

In embodiments, the subject has sepsis or is developing sepsis.

In embodiments, the subject has endotoxemia, septicemia or septic shock.

In embodiments, electrically modulating cholinergic neurons is effected using microelectrodes placed in the subject's central nervous system.

In embodiments, electrically modulating cholinergic neurons is effected using microelectrodes placed externally to the subject's central nervous system.

In embodiments, electrically modulating cholinergic neurons is effected using transcutaneous microelectrodes.

In embodiments, the microelectrodes are positioned stereotactically prior to electrical stimulation.

In embodiments, no other source of vagal nerve activity is artificially electrically stimulated.

A method of artificially reducing TNF release by splenic macrophages expressing α7nAChR in a subject comprising electrically modulating cholinergic neurons in a dorsal motor nucleus of a vagal nerve of subject effective to reduce TNF release by splenic macrophages expressing α7nAChR.

A method of enhancing an inflammatory response in a subject comprising electrically inhibiting activity of cholinergic neurons in a dorsal motor nucleus of a vagal nerve of the subject effective to enhance an inflammatory response in a subject.

A method of increasing serum TNF levels in a subject comprising electrically inhibiting activity of cholinergic neurons in a dorsal motor nucleus of a vagal nerve of the subject effective to increase serum TNF levels in a subject.

In embodiments, the electrically modulating is electrically stimulating.

In embodiments, the inflammation is an inflammatory condition. Inflammatory conditions include sepsis. Other inflammatory conditions include ankylosing spondylitis (AS), antiphospholipid antibody syndrome (APS), gout, inflammatory arthritis, myositis, rheumatoid arthritis, scleroderma, Sjogren's syndrome, systemic lupus erythematosus (SLE, lupus), and vasculitis, and autoimmune diseases generally.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

Optogenetics allows for neurotransmitter-specific fiber activation (27) in a way that is impossible with traditional techniques. Using this method, the cholinergic component of the vagus nerve is shown to be sufficient to activate the inflammatory reflex.

The inventors hypothesized that the vagus nerve and splenic nerve form a synapse and that this functions as a key feature of the inflammatory reflex pathway. It is generally accepted that spleen is innervated by a single unidirectional efferent adrenergic nerve (29), which, at least in part, receives vagal inputs based on anatomical (30) and pharmacological (15, 16) studies. However, controversy still exists, specifically regarding the impact—and even existence—of vagal modulation of splenic immunologic function (31-38). By using fluorescence imaging and neural recording methods, it is demonstrated herein that the vagus and splenic nerves form a functional synapse that relays information from the brainstem to the spleen.

It is hypothesized that efferent signals originating in the DMV are carried by cholinergic fibers in the vagus nerve and synapse in the celiac ganglion onto the splenic nerve. Thesis signals are sufficient to regulate systemic inflammation in response to endotoxemia in a mouse model.

Results

To investigate the hypothesis that that the celiac ganglion is necessary for an intact inflammatory reflex, celiac ganglionectomies were first performed on wild-type C57Bl/6 mice. Following the removal of the left celiac ganglion, mice were allowed to recover. Of the 10 mice that underwent ganglionectomy, three did not survive the full week. Ten age-matched mice that did not undergo ganglionectomy were used as controls. After one week, all animals were given LPS to induce an inflammatory response. There was no difference in the ratio of spleen to total body weight in either group nor systemic TNF in serum. However, in those mice without the left celiac ganglion, there was a significantly higher level of TNF in the spleen when compared to control mice.

Using commercially available transgenic mice expressing channelrhodopsin (ChR2) tagged with enhanced yellow fluorescent protein (EYFP) under the choline acetyltransferase promoter (ChAT-ChR2-EYFP, Jackson #014546) (39, 40), it was first sought to characterize the expression of ChR2 in the brainstem. There was robust expression of ChR2-EYFP on the surfaces of ChAT+ cells in the DMV and no expression in littermate controls.

Prior to performing optogenetic stimulation, successful repeated fiber optic probe placement was confirmed. Initial experiments were performed using by injecting 100 μL of 1% solution of 1,1'-Dioctadecyl-3,3,3',3'-Tetramethylindocarbocyanine Perchlorate (DiI) into the left DMV). Coordinates were confirmed with a standard mouse brain atlas. Additional intra-operative confirmation was performed during optogenetic stimulation. Bradycardia was observed on electrocardiogram (EKG) with light stimulation (200 μm fiber optic probe, 473 nm, 20 Hz, 25% duty cycle, 8-12 mW, 2 minutes) with interval increases in heart rate once stimulation ceased (see FIG. 1 for bradycardia effect).

DMV Cholinergic Input to the Heart was Confirmed Via Viral Tracing Studies.

Next, to study the efferent signals from the DMV to the spleen, a transgenic mouse was developed that expressed both a green fluorescent protein under the ChAT promoter and a tomato fluorescent protein under the control of the tyrosine hydroxylase promoter (TH-Tomato ChAT-GFP). Using this mouse, identification of the left celiac ganglion could be confirmed by visualizing the co-localization of green cholinergic and red adrenergic tissue. However, because these fluorescent proteins were not restricted to neuronal tissue, additional viral tracing studies were conducted.

Adeno-associated virus serotype 9 that was engineered to express both channelrhodopsin and yellow fluorescent protein (AAV9-ChR2-EYFP) was injected into the DMV of a synapsin-cre mouse in which cre recombinase is expressed in all neural tissue. Additionally, herpes virus that expressed channelrhodopsin and mCherry fluorescent protein (HSV-ChR2-mCherry) was injected into the splenic parenchyma of the same mouse. After a one month incubation period, the left celiac ganglion was isolated, sectioned, and analyzed for immunofluorescence. Staining for NeuN confirmed the presence of neuronal tissue in the isolated ganglion, and the presence of green axonal fibers in proximity to red cell bodies provided strong evidence for a vagus/splenic nerve synapse. Separate staining for the neuronal synaptic marker synaptophysin also demonstrated apparent synapses between the vagus and splenic nerves.

Next, to determine the specific contribution of cholinergic neurons originating in the DMV on the inflammatory reflex, optogenetic stimulation was performed on ChAT-ChR2-EYFP mice. As it was demonstrated that the vagus and splenic nerves are in close proximity, it was sought to test the hypothesis that there is a functional synapse between the vagus and splenic nerves. To do this, splenic nerve activity was recorded during DMV optogenetic stimulation. In littermate controls, DMV optogenetic stimulation did not increase splenic nerve activity over baseline, whereas in ChAT-ChR2-EYFP mice, increased splenic nerve activity was observed coinciding with DMV optogenetic stimulation. In a subset of animals, the left cervical vagus nerve was exposed and 0.05% bupivacaine was administered directly to the nerve. In these animals, subsequent DMV stimulation failed to increase splenic nerve activity over baseline.

Figure 2:
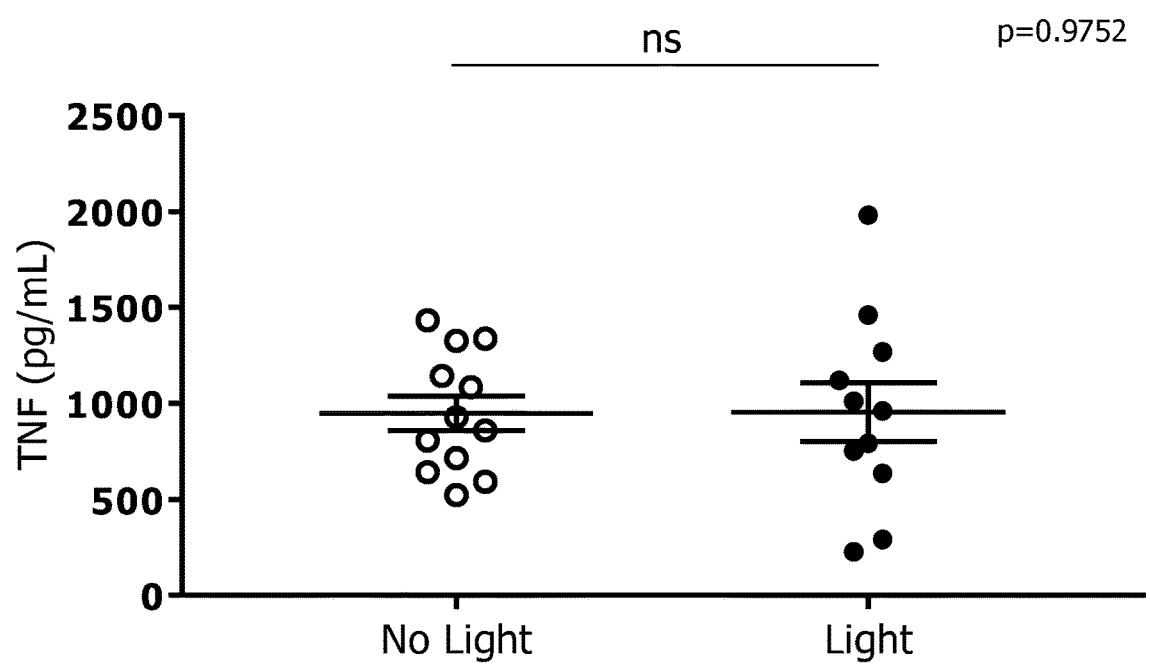
FIG. 2: Optogenetic stimulation of the cholinergic neurons in the DMV fail to suppress systemic TNF levels in littermate controls during endotoxemia. Littermate control mice were exposed to either optogenetic stimulation (n=11) or no light (n=12) for five minutes (473 nm laser, 20 Hz, 25% duty cycle). After 24 h, animals were challenged with endotoxin. Levels of serum TNF were analyzed 90 min post-endotoxin challenge.
Figure 3:
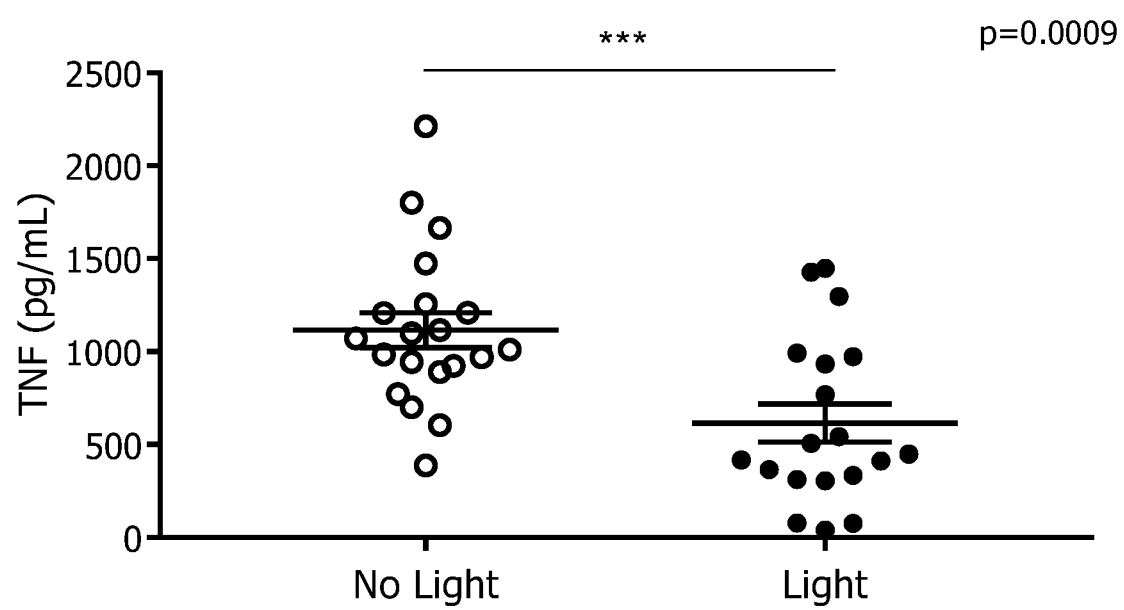
FIG. 3: Optogenetic stimulation of the cholinergic neurons in the DMV attenuates systemic TNF levels in endotoxemia. ChAT-ChR2 mice were exposed to either optogenetic stimulation (n=19) or no light (n=20) for five minutes (473 nm laser, 20 Hz, 25% duty cycle). After 24 h, animals were challenged with endotoxin. Levels of serum TNF were analyzed 90 min post-endotoxin challenge. (p=0.0009)
Figure 4:
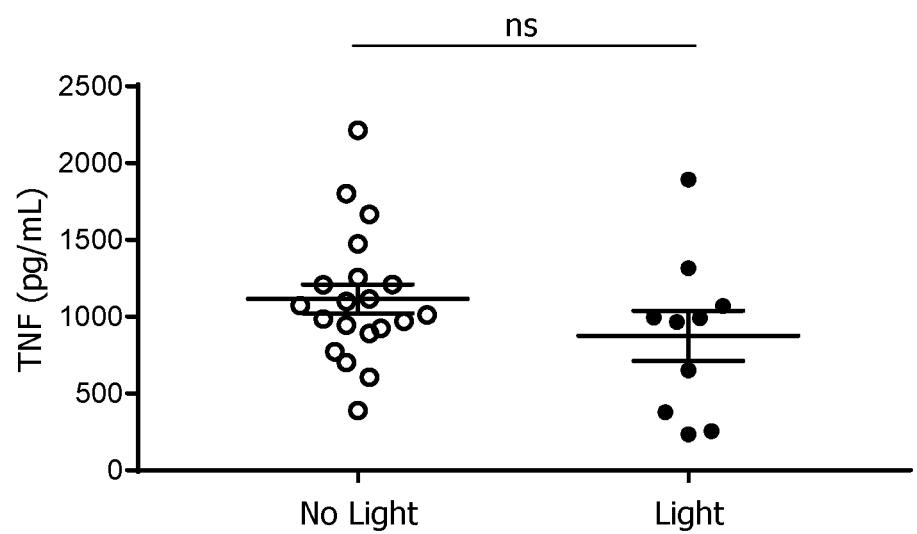
FIG. 4: Optogenetic stimulation with a 593.5 nm laser has no effect on inflammatory response in ChAT-ChR2-EYFP mice. ChAT-ChR2 mice were exposed to 593.5 nm laser (not specific for ChR2) or no light (n=11/group) for five minutes (473 nm laser, 20 Hz, 25% duty cycle). After 24 h, animals were challenged with endotoxin. Levels of serum TNF were analyzed 90 min post-endotoxin challenge.

Additional studies were performed investigating how DMV optogenetic stimulation impacts the inflammatory response to endotoxin. Following DMV optogenetic stimulation, mice were allowed to recover for 24 hours, at which time lipopolysaccharide (LPS) was given via intraperitoneal injection. Blood was then collected and the serum isolated for TNF measurement. In littermate controls, DMV optogenetic stimulation with blue light had no effect on the inflammatory response to LPS (FIG. 2). In contrast, in ChAT-ChR2-EYFP mice, TNF was significantly decreased in those animals receiving DMV optogenetic stimulation (FIG. 3). Furthermore, as an additional control, yellow light (593.5 nm) optogenetic stimulation failed to alter the inflammatory response to endotoxin in ChAT-ChR2-EYFP mice (FIG. 4).

Discussion

The impact of vagus nerve stimulation on systemic inflammation has been extensively studied and reproduced in laboratories and clinical studies around the world (2, 3, 41). While early clinical trials have shown promising results in various disorders, the underlying mechanisms responsible for the therapeutic effects have not been completely uncovered. Here, to our knowledge, we describe for the first time optogenetic activation of the inflammatory reflex.

Optogenetic stimulation of the DMV in these studies reliably and significantly reduced systemic TNF following endotoxemia, demonstrating that cholinergic neurons originating in the DMV are sufficient to activate the inflammatory reflex. While these experiments do not exclude the possibility of contributions from other neurotransmitters or neurons originating from different regions on the brain, they do demonstrate that activation of this subset of neurons is sufficient to reduce TNF in an animal model of endotoxemia.

There has been debate regarding the involvement of the vagus nerve (37, 42) in the inflammatory reflex, whether the vagus nerve exerts an effect on the splenic nerve (43, 44), and whether that proposed interaction occurs in the celiac ganglion (32). To address these controversies, we systematically studied the efferent arm of the inflammatory reflex from its origins in the DMV to its terminals in the spleen. The findings demonstrate that the efferent arm of the inflammatory reflex originates in the DMV, that the vagus nerve carries signals that directly act on the splenic nerve at the celiac ganglion, and that these signals are sufficient for a reduction in inflammatory cytokines caused by endotoxemia.

To explore the functional role of the celiac ganglion in the inflammatory reflex, the left celiac ganglion was first removed in wild type animals. In these animals, after exposure to LPS, there was a significant increase in splenic TNF compared to intact mice. This dysregulation of the innate inflammatory reflex indicates that the celiac ganglion is critical to the tonic dampening of innate anti-inflammatory mechanisms. The fact that the splenic TNF is increased while serum TNF is not may indicate some previously unknown effect of splenic nerve innervation on TNF release. This result leads us to hypothesize that the celiac ganglion is therefore central to the efferent pathway previously described.

In order to further map this neural connection, we used a number of transgenic animal models. After characterizing the CHR2 expression in commercially available ChAT-ChR2-EYFP mice, we were able to optimize methods for optogenetically stimulating the DMV. Successful placement of the fiber optic probe was demonstrated by both stimulation-induced bradycardia and post-mortem immunofluorescence. The contribution of fibers originating in the DMV to heart rate has historically been controversial (45), but there are a number of historical tracing studies clearly demonstrating the connection between the DMV and heart (46, 47). The current experiments described herein rely on bradycardia only to the extent of confirming fiber optic probe placement. This, combined with brainstem histology clearly shows correct DMV placement.

It was next sought to visualize the synaptic connection between the vagus and splenic nerves. To do this, the celiac ganglion was first identified in TH-Tomato ChAT-GFP mice. In these mice, the celiac ganglion will fluoresce both green (identifying cholinergic cells) and red (identifying adrenergic cells). Because this is not neuronal-specific, this was then repeated in Syn-cre mice with viral tracers. By using a retrograde virus injected into the spleen and an anterograde virus injected into the brainstem, neuronal projections to the celiac ganglion could be identified. After surgical removal, sectioning, and immunofluorescent staining, the close approximation of cholinergic fibers and adrenergic cell bodies could readily be identified. This evidence lends credence to our previous work in which the celiac ganglion was hypothesized to be where the celiac and splenic nerves synapse.

To further characterize these synaptic inputs, experiments were performed in which optogenetic stimulation was applied to the DMV and splenic nerve activity was simultaneously recorded. When bupivacaine, a sodium-channel blocker, was applied to the vagus nerve, the signals recorded in the splenic nerve returned to baseline. This indicates that the signals originating in the DMV are transmitted via the vagus nerve, and that these signals are acting upon the splenic nerve.

Finally, to determine whether these splenic nerve signals are effective in modulating immune responses, optogenetic stimulation was performed in ChAT-ChR2 mice, activating the cholinergic fibers residing in the DMV. After recovery, these animals were given LPS to induce an immune response. In those animals subjected to DMV stimulation, the measured TNF was significantly reduced when compared to sham controls. This demonstrates that the cholinergic subset of the vagus nerve is sufficient to attenuate inflammation in this model of endotoxemia. While previous studies—and human clinical trials—have shown the effectiveness of whole-nerve stimulation, to our knowledge this study represents the first example of optogenetic stimulation of the inflammatory reflex in a fiber-specific manner.

With selective activation of the cholinergic efferent pathway, there was increased splenic nerve activity, resulting in a decreased inflammatory response to endotoxin challenge. Together, these discoveries further our understanding of the inflammatory reflex and demonstrate that cholinergic vagal nerve fibers originating in the DMV can modulate cytokine levels. An understanding of neurotransmitter and fiber-specificity within this neural circuit can potentially lead to more selective bioelectronic therapies to treat patients with chronic inflammatory conditions.

Methods

Animals: Mice expressing channelrhodopsin (ChR2) and enhanced yellow fluorescent protein (EYFP) under the transcriptional control of choline acetyltransferase (ChAT) were obtained from Jackson Laboratories (ChAT-ChR2-EYFP, stock #014546) and bred in-house. Animals were kept at 25° C. on a 12-hour light/dark cycle. Water and regular rodent chow were available ad libitum. All experiments were performed with male mice and were performed under protocols approved by the Institutional Animal Care and Use Committee of the Feinstein Institute for Medical Research, Northwell Health.

Immunohistochemistry: For DMV staining ChAT-ChR2-EYFP mice were euthanized via $CO_2$ asphyxiation and perfused via cardiac puncture with phosphate buffered saline (PBS) followed by 4% paraformaldehyde (PFA). The brain was then removed and fixed overnight in 4% PFA at 4° C. The following day, 50 µm free-floating sections were created using a vibrotome (Leica VT1200 S) and stained for ChAT and EYFP. After a PBS wash, the sections were treated with 0.2% Triton-X 100 for 30 minutes, followed by blocking solution for 2 hours (10% donkey serum, 0.05% Triton-x 100). Primary antibodies were diluted in 2% donkey serum and 0.01% Triton-X 100 and incubated at 4° C. for 3 days. The primary antibodies were: goat anti-ChAT (EMD Millipore #AB144P, 1:200) and rabbit anti-YFP/GFP (Invitrogen #A21311, 1:500). Following a PBS wash, the samples were incubated with the following secondary antibody for one hour at room temperature: donkey anti-goat IgG Alexa Fluor 555 (Thermo Fisher #A-21432, 1:400). After another wash in PBS, the samples were mounted and coverslipped using Vectashield anti-fade mounting medium with DAPI (Vector Laboratories #H-1200). Fluorescence images were acquired on a Zeiss LSM880 confocal microscope and analyzed using FIJI software (48).

For Celiac Ganglion identification additional mice expressing cre recombinase under the tyrosine hydroxylase promoter (Jackson stock #008601) were crossed with cre-dependent tdTomato-expressing mice (Jackson stock #007914). The resultant offspring (TH-tdTomato) were crossed with mice expressing enhanced green fluorescent protein (EGFP) under the transcriptional control of choline acetyltransferase (ChAT) (Jackson stock #007902). The final mouse (TH-TdTomato ChAT-GFP) was used to identify the celiac ganglion by visualizing the gross co-localization of green and red fluorescence in the celiac ganglion using a dissecting fluorescent microscope.

For Celiac Ganglion immunofluorescence mice expressing cre recombinase in neuronal cells under the Synapsin I promoter (Jackson stock #003966) were used.

Brainstem Injections: Mice were anesthetized with a cocktail of ketamine (144 mg/kg) and xylazine (13 mg/kg) based on weight. After appropriate depth of anesthesia was assessed by a lack of toe pinch reflex, the back of the head was shaved and Nair™ was applied to remove excess hair. The mouse was placed in a stereotactic frame and held in place with bilateral ear bars. The head was tilted down 45° to lift the cerebellum off the brainstem and allowing for visualization of the $4^{th}$ ventricle. A midline incision was made and the subcutaneous tissue and paraspinal muscles were retracted laterally, exposing the dura mater. A 23G needle bent at 45° was used to incise the dura mater, taking care not to injure the underlying brainstem nor vessels. After the cerebrospinal fluid (CSF) was cleared, the base of the fourth ventricle and obex were identified. A glass micropipette (FIVEphoton Biochemicals™ #MGM-1B-10-100) was used to inject AAV-ChR2-EYFP (Penn Vector Core Gene Therapy Program. AAV5.EF1a.DIO.hChR2(H134R)-eYFP.WPRE.hGH[Addgene20298P]) into the DMV. Using the obex as a reference point, the micropipette was moved lateral 0.25 mm to the left and 0.48 mm deep into the tissue into the dorsal motor nucleus of the vagus nerve (DMV). Approximately 40 nL total virus was injected into the DMV using a Picospritzer III microinjection dispense system (Parker #052-0500-900) (20 injections of approximately 2 nL each at 3 PSI and 10 ms duration). Following injection, the micropipette was slowly removed to avoid contamination.

Splenic Injections: While still under anesthesia, the abdomen was shaved using an electric razor, and a midline incision was made. The spleen was identified and retracted towards the midline. A separate glass micropipette containing HSV1-ChR2-mCherry (Gene Delivery Technology Core. MGH Neurology. hEF1a-LS1L-hChR2[H134R]-mCherry) was used to inject approximately 60 nL virus (20 injections of approximately 2 nL each at 3 PSI and 10 ms duration) into the splenic parenchyma. Following injection, the micropipette was slowly removed and the midline incision was closed in two layers with 5-0 vicryl sutures.

Mice were allowed to recover for 1 month, at which point they were euthanized for examination. The mice was perfused via cardiac puncture first with 20 mL PBS then with 20 mL 4% PFA. The left celiac ganglion was then excised and post-fixed for 30 minutes in 4% PFA then overnight in 30% sucrose. It was then embedded in optimal cutting temperature (OCT) compound on dry ice. 16 µm frozen sections were produced using a cryostat (Microm HM 505N), and sections were mounted on slides for staining. The tissue was then incubated for 48 hours at 4° C. with primary antibodies diluted in staining solution (PBS, 0.2% Triton-X 100, and 0.1% normal goat serum) and then for 2 hours at room temperature with secondary antibodies. Neuronal tissue was detected using mouse anti-NeuN (Millipore Sigma MAB377) with goat anti-mouse DyLight 650 (Abcam 97018) and mouse anti-synaptophysin (Abcam 8049) with donkey anti-mouse Alexa Fluor 680 (Thermo Fisher A10038) antibodies. EGFP was detected using rabbit anti-GFP-Alexa Fluor 288 (Thermo Fisher A-21311) antibodies. Tissue was then washed, mounted on slides, and coverslipped with SouthernBiotech Dapi-Fluoromount-G Clear Mounting Media (Fisher OB010020). All images were analyzed using FIJI software (48).

Brainstem Optogenetics: Mice were anesthetized with a cocktail of ketamine (144 mg/kg) and xylazine (13 mg/kg) based on weight. After appropriate depth of anesthesia was assessed by a lack of toe pinch reflex, the back of the head was shaved and Nair™ was applied to remove excess hair. The mouse was placed in a stereotactic frame and held in place with bilateral ear bars. The head was tilted down 45° to lift the cerebellum off the brainstem and allowing for visualization of the $4^{th}$ ventricle. A midline skin incision was made and the subcutaneous tissue and paraspinal muscles were retracted laterally, exposing the dura mater. A 23G needle bent at 45° was used to incise the dura mater, taking care not to injure the underlying brainstem nor vessels. After the cerebrospinal fluid (CSF) was cleared, the base of the fourth ventricle and obex were identified. The fiber optic probe was moved laterally 0.25 mm to the obex and 0.48 mm deep into the brainstem tissue into the DMV. Light stimulation was delivered via a 200 µm fiber optic cannula (Thorlabs #CFMC12L05) connected to a blue laser source (Opto Engine LLC #MBL-F-473). Stimulation (20 Hz, 25% duty cycle, 5 minute duration) was maintained between 7-15 mW at the probe tip. Following optogenetic stimulation, the probe was removed and the wound was approximated in two layers using 5-0 vicryl sutures (Ethicon #J385H). After closure, the wound was covered with tissue adhesive (Vetbond #1469SB). Mice were placed on a heat pad until fully recovered, at which time they were returned to the colony room.

Splenic Nerve Recording: Once the mouse was positioned in a stereotactic frame as described above and a fiber optic probe was inserted into the DMV, a 2 cm oblique incision was made on the left flank just inferior to the diaphragm, and the peritoneal cavity was entered. The spleen was extracorporealized and reflected rostrally, exposing the hilar vasculature. The pancreas and abdominal adipose tissue were dissected away from the splenic neurovascular bundle and a bipolar cuff electrode was placed. Data was acquired at 30 kHz using the OmniPlex® Neural Data Acquisition System (Plexon) and analyzed offline using Spike2 (Cambridge Electronic Design Limited).

Endotoxemia: For all endotoxemia experiments, a stock solution of lipopolysaccharide (LPS) from *Escherichia coli* 0111:B4 (Sigma-Aldrich #L5293) was kept at −20° C. at a concentration of 1 mg/mL. Prior to use, the stock solution was thawed and diluted 1:32 and sonicated to prevent adhesion of LPS molecules. LPS was administered via IP injection to each mouse at a dose of 0.25 mg/kg. Ninety minutes following injection, the mice were euthanized and blood was collected and allowed to clot at room temperature for 30 minutes. The blood was then centrifuged at 5000 RPM for 10 minutes and the supernatant isolated. This was then spun at 10000 RPM for 2 minutes, leaving debris-free serum. This serum was then analyzed for tumor necrosis factor (TNF) using a commercially available ELISA (Invitrogen #88-7324-22).

REFERENCES

1. Johnson, R. L. & Wilson, C. G. A review of vagus nerve stimulation as a therapeutic intervention. J. Inflamm. Res. 11, 203-213 (2018).
2. Bonaz, B., Sinniger, V. & Pellissier, S. Vagus nerve stimulation: a new promising therapeutic tool in inflammatory bowel disease. J. Intern. Med. 282, 46-63 (2017).
3. Koopman, F. A. et al. Vagus nerve stimulation inhibits cytokine production and attenuates disease severity in rheumatoid arthritis. Proc. Natl. Acad. Sci. U.S.A. 113, 8284-9 (2016).
4. Bernik, T. R. et al. Pharmacological Stimulation of the Cholinergic Antiinflammatory Pathway. J. Exp. Med. 195, 781-788 (2002).
5. Borovikova, L. V et al. Vagus nerve stimulation attenuates the systemic inflammatory response to endotoxin. Nature 405, 458-62 (2000).
6. Huston, J. M. et al. Splenectomy protects against sepsis lethality and reduces serum HMGB1 levels. J. Immunol. 181, 3535-3539 (2008).
7. Wang, H. et al. Cholinergic agonists inhibit HMGB1 release and improve survival in experimental sepsis. Nat. Med. 10, 1216-1221 (2004).
8. Kessler, W. et al. The vagal nerve as a link between the nervous and immune system in the instance of polymicrobial sepsis. Langenbeck's Arch. Surg. 391, 83-87 (2006).
9. Bianchi, M. et al. Suppression of proinflammatory cytokines in monocytes by a tetravalent guanylhydrazone. J. Exp. Med. 183, 927-36 (1996).
10. Watkins, L. R. et al. Blockade of interleukin-1 induced hyperthermia by subdiaphragmatic vagotomy: evidence for vagal mediation of immune-brain communication. Neurosci. Lett. 183, 27-31 (1995).
11. Zanos, T. P. et al. Identification of cytokine-specific sensory neural signals by decoding murine vagus nerve activity. 115, (2018).
12. Lori, A., Perrotta, M., Lembo, G. & Carnevale, D. The spleen: A hub connecting nervous and immune systems in cardiovascular and metabolic diseases. Int. J. Mol. Sci. 18, (2017).
13. Rosas-Ballina, M. et al. Splenic nerve is required for cholinergic antiinflammatory pathway control of TNF in endotoxemia. Proc. Natl. Acad. Sci. U.S.A. 105, 11008-13 (2008).
14. Huston, J. M. et al. Splenectomy inactivates the cholinergic antiinflammatory pathway during lethal endotoxemia and polymicrobial sepsis. J. Exp. Med. 203, 1623-8 (2006).
15. Downs, A. M., Bond, C. E. & Hoover, D. B. Localization of alpha7 nicotinic acetylcholine receptor mRNA and protein within the cholinergic anti-inflammatory pathway. Neuroscience 266, 178-185 (2014).
16. Vida, G., Pena, G., Deitch, E. A. & Ulloa, L. 7-Cholinergic Receptor Mediates Vagal Induction of Splenic Norepinephrine. J. Immunol. 186, 4340-4346 (2011).
17. Fujii, T. et al. Expression and function of the cholinergic system in immune cells. Front. Immunol. 8, 1-18 (2017).
18. Rosas-Ballina, M. et al. Acetylcholine-synthesizing T cells relay neural signals in a vagus nerve circuit. Science 334, 98-101 (2011).
19. Wang, H. et al. Nicotinic acetylcholine receptor alpha7 subunit is an essential regulator of inflammation. Nature 421, 384-388 (2003).
20. Olofsson, P. S. et al. α 7 Nicotinic Acetylcholine Receptor (α 7nAChR) Expression in Bone Marrow—Derived Non—T Cells Is Required for the Inflammatory Reflex. 539-543 (2012). doi:10.2119/molmed.2011.00405
21. de Jonge, W. J. et al. Stimulation of the vagus nerve attenuates macrophage activation by activating the Jak2-STAT3 signaling pathway. Nat. Immunol. 6, 844-51 (2005).
22. Rosas-ballina, M. et al. Splenic nerve is required for cholinergic antiinflammatory pathway control of TNF in endotoxemia. (2008).
23. Matteoli, G. & Boeckxstaens, G. E. The vagal innervation of the gut and immune homeostasis. Gut 62, 1214-1222 (2013).
24. Chang, R. B., Strochlic, D. E., Williams, E. K., Umans, B. D. & Liberles, S. D. Vagal sensory neuron subtypes that differentially control breathing. Cell 161, 622-633 (2015).
25. Pavlov, V. A. et al. Brain acetylcholinesterase activity controls systemic cytokine levels through the cholinergic anti-inflammatory pathway. Brain. Behav. Immun. 23, 41-45 (2009).
26. Abe, C. et al. C1 neurons mediate a stress-induced anti-inflammatory reflex in mice. Nat. Neurosci. 20, 700-707 (2017).
27. Boyden, E. S., Zhang, F., Bamberg, E., Nagel, G. & Deisseroth, K. Millisecond-timescale, genetically targeted optical control of neural activity. Nat. Neurosci. 8, 1263-1268 (2005).
28. Andersson, U. & Tracey, K. J. Neural reflexes in inflammation and immunity. J. Exp. Med. 209, 1057-1068 (2012).

29. Nance, D. M. & Sanders, V. M. Autonomic innervation and regulation of the immune system (1987-2007). Brain. Behav. Immun. 21, 736-45 (2007).
30. Berthoud, H. R. & Powley, T. L. Interaction between parasympathetic and sympathetic nerves in prevertebral ganglia: Morphological evidence for vagal efferent innervation of ganglion cells in the rat. Microsc. Res. Tech. 35, 80-86 (1996).
31. Gautron, L. et al. Neuronal and nonneuronal cholinergic structures in the mouse gastrointestinal tract and spleen. J. Comp. Neurol. 521, 3741-67 (2013).
32. Bratton, B. O. et al. Neural regulation of inflammation: No neural connection from the vagus to splenic sympathetic neurons. Exp. Physiol. 97, 1180-1185 (2012).
33. Kooijman, S. et al. Splenic autonomic denervation increases inflammatory status but does not aggravate atherosclerotic lesion development. Am. J. Physiol.—Hear. Circ. Physiol. 309, H646-H654 (2015).
34. Murray, K. et al. Neuroanatomy of the spleen: Mapping the relationship between sympathetic neurons and lymphocytes. PLoS One 12, 1-17 (2017).
35. McAllen, R. M., Cook, A. D., Khiew, H. W., Martelli, D. & Hamilton, J. A. The interface between cholinergic pathways and the immune system and its relevance to arthritis. Arthritis Res. Ther. 17, 1-9 (2015).
36. Fuentes, J. M., Hanly, E. J., Aurora, A. R., De Maio, A. & Talamini, M. A. Anesthesia-specific protection from endotoxic shock is not mediated through the vagus nerve. Surgery 138, 766-771 (2005).
37. Martelli, D., Yao, S. T., McKinley, M. J. & McAllen, R. M. Reflex control of inflammation by sympathetic nerves, not the vagus. J. Physiol. 592, 1677-86 (2014).
38. Buijs, R. M., Van der Vliet, J., Garidou, M. L., Huitinga, I. & Escobar, C. Spleen vagal denervation inhibits the production of antibodies to circulating antigens. PLoS One 3, 1-8 (2008).
39. Zhao, S. et al. Cell type—specific channelrhodopsin-2 transgenic mice for optogenetic dissection of neural circuitry function. Nat. Methods 8, 745-52 (2011).
40. Kolisnyk, B. et al. ChAT-ChR2-EYFP mice have enhanced motor endurance but show deficits in attention and several additional cognitive domains. J. Neurosci. 33, 10427-38 (2013).
41. Huston, J. M. The vagus nerve and the inflammatory reflex: wandering on a new treatment paradigm for systemic inflammation and sepsis. Surg Infect 13, 187-193 (2012).
42. Griton, M. & Konsman, J. P. Neural pathways involved in infection-induced inflammation: recent insights and clinical implications. Clin. Auton. Res. 1-11 (2018). doi: 10.1007/s10286-018-0518-y
43. Bratton, B. O. et al. Neural regulation of inflammation: no neural connection from the vagus to splenic sympathetic neurons. Exp. Physiol. 97, 1180-5 (2012).
44. Martelli, D., McKinley, M. J. & McAllen, R. M. The cholinergic anti-inflammatory pathway: A critical review. Auton. Neurosci. Basic Clin. 182, 65-69 (2014).
45. Standish, A., Enquist, L. W., Escardo, J. A., Schwaberl, J. S. & Schwaber, J. S. Central Neuronal Circuit Innervating the Rat Heart Defined by Transneuronal Transport of Pseudorabies Virus. J. Neurosci. 15, 1998-2012 (1995).
46. Calaresu, B. Y. F. R. & Cottle, M. K. ORIGIN OF CARDIOMOTOR FIBRES IN THE DORSAL NUCLEUS OF THE VAGUS IN THE CAT: A HISTOLOGICAL STUDY From the Department of Physiology, University of Alberta, have indicated that visceral motor cells of the vagus nerve are located In contrast with these re. 252-260 (1965).
47. Gourine, A. V., Machhada, A., Trapp, S. & Spyer, K. M. Cardiac vagal preganglionic neurones: An update. Auton. Neurosci. Basic Clin. 199, 24-28 (2016).
48. Schindelin, J. et al. Fiji: An open-source platform for biological-image analysis. Nat. Methods 9, 676-682 (2012).

What is claimed is:

1. A method of suppressing or ameliorating inflammation in a subject comprising selectively electrically stimulating cholinergic neurons in a dorsal motor nucleus of a vagal nerve of the subject, wherein no other source of vagal nerve activity is artificially electrically stimulated and effective to induce splenic nerve activity suppression of TNF release so as to suppress or ameliorate inflammation in a subject.

2. The method of claim 1, wherein the method effects an increase in splenic norepinephrine release.

3. The method of claim 1, wherein the subject is human.

4. The method of claim 1, wherein the subject has sepsis or is developing sepsis.

5. The method of claim 1, wherein the subject has endotoxemia, septicemia or septic shock.

6. The method of claim 1, wherein electrically stimulating is effected using microelectrodes placed in the subject's central nervous system.

7. The method of claim 6 wherein the microelectrodes are positioned stereotactically prior to electrical stimulation.

* * * * *